US006676957B1

(12) United States Patent
Resheski-Wedepohl et al.

(10) Patent No.: US 6,676,957 B1
(45) Date of Patent: Jan. 13, 2004

(54) NON-ABSORBENT SUBSTRATES FOR THE INHIBITION OF EXOPROTEIN PRODUCTION FROM GRAM POSITIVE BACTERIA

(75) Inventors: Kim L. Resheski-Wedepohl, Reedsville, WI (US); Rae Ellen Syverson, Fond du Lac, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/724,023

(22) Filed: Nov. 28, 2000

(51) Int. Cl.[7] .............................. A61K 7/16; A61K 9/06
(52) U.S. Cl. ..................... 424/430; 424/431; 514/967; 514/843; 514/841
(58) Field of Search ............................. 424/430, 431; 514/967, 843, 841

(56) References Cited

U.S. PATENT DOCUMENTS

| | | | |
|---|---|---|---|
| 4,405,323 A | 9/1983 | Auerbach .................... 604/285 |
| 4,413,032 A | 11/1983 | Hartmann et al. ........... 428/288 |
| 4,413,986 A | 11/1983 | Jacobs .......................... 604/14 |
| 4,424,054 A | 1/1984 | Conn et al. .................... 604/11 |
| 4,431,427 A | 2/1984 | Lefren et al. ................. 604/285 |
| 4,585,792 A | 4/1986 | Jacob et al. .................. 514/474 |
| 4,722,936 A | * 2/1988 | Jacob .......................... 514/474 |
| 4,722,937 A | 2/1988 | Jacob et al. .................. 514/474 |
| 4,769,021 A | 9/1988 | Kass .......................... 604/367 |
| 4,952,211 A | 8/1990 | Snider ......................... 604/285 |
| 5,000,749 A | 3/1991 | LeVeen et al. ............... 604/904 |
| 5,070,889 A | 12/1991 | LeVeen et al. ............... 124/830 |
| 5,071,648 A | 12/1991 | Rosenblatt ................. 424/78.06 |
| 5,156,164 A | 10/1992 | LeVeen et al. ............... 128/832 |
| 5,221,693 A | 6/1993 | Shetty ......................... 514/635 |
| 5,270,032 A | 12/1993 | Pollock et al. |
| 5,342,331 A | 8/1994 | Silber et al. ................. 604/330 |
| 5,389,374 A | 2/1995 | Brown-Skrobot ........... 424/431 |
| 5,476,455 A | 12/1995 | Silber ......................... 604/330 |
| 5,498,252 A | 3/1996 | Silber ......................... 604/330 |
| 5,527,892 A | 6/1996 | Borsotti et al. ............. 536/18.6 |
| 5,540,979 A | 7/1996 | Yahiaoui et al. ............. 428/212 |
| 5,547,985 A | 8/1996 | Brown-Skrobot et al. .. 514/546 |
| 5,601,814 A | 2/1997 | Barton et al. ............... 424/85.2 |
| 5,612,045 A | 3/1997 | Syverson ..................... 424/402 |
| 5,618,554 A | 4/1997 | Syverson ..................... 424/431 |
| 5,641,503 A | 6/1997 | Brown-Skrobot ........... 424/431 |
| 5,679,369 A | 10/1997 | Brown-Skrobot ........... 424/431 |
| 5,685,872 A | 11/1997 | Syverson ..................... 604/360 |
| 5,705,182 A | 1/1998 | Brown-Skrobot ........... 424/431 |
| 5,719,113 A | 2/1998 | Fendler et al. |
| 5,753,252 A | 5/1998 | Brown-Skrobot ........... 424/431 |
| 5,770,543 A | 6/1998 | Garst et al. .................. 504/116 |
| 5,814,567 A | 9/1998 | Yahiaoui et al. ............. 442/118 |
| 5,817,047 A | 10/1998 | Osborn, III et al. .......... 604/14 |
| 5,932,495 A | 8/1999 | Boney et al. ................. 442/121 |
| 5,945,175 A | 8/1999 | Yahiaoui et al. ............. 427/534 |
| 6,017,832 A | 1/2000 | Yahiaoui et al. ............. 442/118 |
| 6,028,016 A | 2/2000 | Yahiaoui et al. ............. 442/118 |
| 6,039,716 A | 3/2000 | Jessup et al. ............. 604/385.1 |
| 6,060,636 A | * 5/2000 | Yahiaoui et al. ............. 604/367 |
| 6,063,335 A | * 5/2000 | Pirolo et al. ................... 422/28 |
| 6,107,268 A | 8/2000 | Yahiaoui et al. ............. 510/438 |
| 6,149,934 A | * 11/2000 | Krzysik et al. .............. 424/404 |
| 6,159,924 A | 12/2000 | Weller et al. |
| 6,177,367 B1 | 1/2001 | Mathis |
| 6,231,557 B1 | 5/2001 | Krautkramer et al. |
| 6,296,936 B1 | * 10/2001 | Yahiaoui et al. ............. 428/375 |
| 6,350,711 B1 | 4/2002 | Potts et al. |
| 6,410,039 B1 | * 6/2002 | Walker ........................ 424/404 |

FOREIGN PATENT DOCUMENTS

| | | |
|---|---|---|
| EP | 0 009 977 A1 | 4/1980 |
| EP | 0 053 221 A2 | 6/1982 |
| EP | 0 110 793 B1 | 6/1984 |
| EP | 0 391 741 A2 | 10/1990 |
| EP | 0 395 099 A2 | 10/1990 |
| EP | 0 483 812 B1 | 5/1992 |
| EP | 0 483 835 A1 | 5/1992 |
| EP | 0 683 260 A2 | 11/1995 |
| GB | 1068667 | 5/1967 |
| WO | WO 87/03208 | 6/1987 |
| WO | WO 94/22501 | 10/1994 |
| WO | WO 98/09662 | 3/1998 |
| WO | WO 98/41179 | 9/1998 |
| WO | WO 99/12505 | 3/1999 |
| WO | WO99/61079 | 12/1999 |

OTHER PUBLICATIONS

Bohach et al., Staphylococcal and Streptococcal Pyrogenic Toxins Involved in Toxin Shock Syndrome and Related Illnesses, Microbiology, 1990, 17(4): 251–272.

Projan, et al., Glycerol Monolaurate Inhibits the Production of β–Lactamase, Toxin Shock Syndrome Toxin–1, and Other Staphylococcal Exoproteins by Interfacing with Signal Transduction, J. Bacteriology Jul., 1994, 176: 4204–4209.

* cited by examiner

*Primary Examiner*—Thurman K. Page
*Assistant Examiner*—Rachel M. Bennett
(74) *Attorney, Agent, or Firm*—Senniger, Powers, Leavitt & Roedel

(57) ABSTRACT

Non-absorbent substrates for use in inhibiting the production of exoproteins from Gram positive bacteria, such as harmful proteins produced by Staphylococcus species, are provided. The substrates are particularly useful for inhibiting the production of TSST-1, alpha-toxin and/or enterotoxins A, B and C from *S. aureus* bacteria. The substrates include an alkyl polyglycoside incorporated in or on at least a portion of the substrate. The alkyl polyglycoside typically has an HLB of about 10 to 15 and/or an average number of carbon atoms in the alkyl chain of about 8 to about 12.

21 Claims, No Drawings

NON-ABSORBENT SUBSTRATES FOR THE INHIBITION OF EXOPROTEIN PRODUCTION FROM GRAM POSITIVE BACTERIA

BACKGROUND

Some microbial products may affect the human host. For example, Staphylococcus aureus (S. aureus) can produce and excrete into its environment a variety of exoproteins including enterotoxins, Toxic Shock Syndrome Toxin-1 (TSST-1), and enzymes such as proteases and lipase. S. aureus is found in the vagina of approximately 16% of healthy women of menstrual age. Approximately 25% of the S. aureus isolated from the vagina are capable of producing TSST-1. TSST-1 and some of the staphylococcal enterotoxins have been identified as causing Toxic Shock Syndrome (TSS) in humans.

Menstrually occurring toxic shock syndrome (TSS), a severe and sometimes fatal multi-system disease, is associated with colonization by Staphylococcus aureus. This disease has been associated with the use of tampons during menstruation. The disease is caused by toxic shock syndrome toxin-1 ("TSST-1") and other staphylococcal enterotoxins.

Symptoms of TSS generally include fever, diarrhea, vomiting and a rash followed by a rapid drop in blood pressure. Systemic vital organ failure occurs in approximately 6% of those who contact the disease. S. aureus does not initiate TSS as a result of the invasion of the microorganism into the vaginal cavity. Instead as S. aureus grows and multiplies, it can produce TSST-1. Only after entering the bloodstream does the TSST-1 toxin act systemically and produce the symptoms attributed to Toxic Shock Syndrome.

There have been numerous attempts to reduce or eliminate pathogenic microorganisms and menstrually occurring TSS by incorporating into a tampon pledget one or more biostatic, biocidal, and/or detoxifying compounds. For example, L-ascorbic acid has been applied to a menstrual tampon to detoxify toxin found in the vagina of the human female during menstruation.

Others have incorporated monoesters and diesters of polyhydric aliphatic alcohols and a fatty acid containing from 8 to 18 carbon atoms. For example, glycerol monolaurate (GML) has been used to retard the production of S. aureus enterotoxins and TSST-1. However, as noted above, esterase is abundantly present in the vaginal epithelium and menstrual fluid. This esterase, in combination with esterase and lipase produced by, bacteria can enzymatically degrade the esters into non-effective compounds. Thus, one or more ester compounds may have to be added to the absorbent article, such as a tampon pledget, in sufficiently high concentrations to detrimentally effect the normal flora present in the vaginal area. When the natural condition is altered, overgrowth by pathogen(s) may take place resulting in a condition known as vaginitis. The use of other non-ionic surfactants, such as alkyl ethers, alkyl amine and alkyl amides, has been reported as a means of avoiding the problem of degradation by esterase (see, e.g., U.S. Pat. Nos. 5,685,872; 5,618,554 and 5,612,045).

Accordingly, there continues to exist a need for agents that will effectively inhibit the production of exoproteins, such as TSST-1, from Gram positive bacteria. The material may be coated on a non-absorbent substrate or have the agent incorporated in other forms, e.g., or in the form of an absorbent product or formulated with a pharmaceutically acceptable carrier. Such agents preferably would be substantially unaffected by the enzymes lipase and esterase and, in addition, should not substantially alter the natural flora found in the vaginal area. The selection of active compounds to inhibit the production of exoproteins is not so readily apparent as some surface active compounds, such as block copolymers of propylene oxide and ethylene oxide, can stimulate toxin production by Gram positive bacteria.

SUMMARY

It has been found that alkyl polyglycoside compounds can inhibit the production of exoprotein(s) of Gram positive bacterium. Exposure to effective amounts of the alkyl polyglycoside(s) can inhibit the production of harmful toxins, such as those produced by Staphylococcus and/or Streptococcal species. For example, alkyl polyglycoside(s) can be utilized to inhibit the production of TSST-1, alpha toxin and/or enterotoxins A, B and C from *S. aureus* bacterium. The alkyl polyglycoside typically has an hydrophilic/lipophilic balance ("HLB") of at least about 10 and/or an average number of carbon atoms in the alkyl chain of about 8 to about 12. The alkyl polyglycoside may be used alone or in combination with one or more other surface active agents, e.g., in combination with compounds such as myreth-3-myristate, glycerol monolaurate and/or laureth-4.

The present invention relates to non-absorbent substrates for use in inhibiting the production of exoproteins from Gram positive bacteria. The substrates are particularly useful for inhibiting the production of TSST-1, alpha-toxin and/or enterotoxins A, B and C from *S. aureus* bacteria. Examples of suitable non-absorbent substrates which have alkyl polyglycoside incorporated in or on at least a portion of the device include non-absorbent incontinence devices, barrier birth control devices and contraceptive sponges. One example of a non-absorbent incontinence device is a female barrier incontinence device, such as an incontinence pledget formed from a resilient material like rubber. Another suitable a non-absorbent substrate is the applicator used with a tampon. For example, the applicator may have alkyl polyglycoside coated on an outer surface, such that when the applicator is used to introduce a tampon into a women's vagina alkyl polyglycoside (e.g., formulated in a cream or wax) is transferred from the applicator onto the wall of the vagina. The non-absorbent substrates typically contain at least about 3 wt. % and, preferably, about 5 to about 10 wt. % alkyl polyglycoside (as add-on wt. %).

The present alkyl polyglycosides are materials which, when exposed to *S. aureus* or other Gram positive bacteria in absorbent products, can reduce the production of exoproteins, such as TSST-1 toxin. It is also believed that the active compounds in the compositions of this invention are effective in combating the production of other types of bacterial toxins, in particular, alpha toxin and Staphylcoccal enterotoxins A, B, and C. The alkyl polyglycosides described herein are also effective at inhibiting the production with respect to these aforementioned exoproteins when the active compound is placed on an absorbent material or caused to come into contact Gram positive bacterium in other forms, e.g., when formulated with a pharmaceutically acceptable carrier or incorporated in or on a non-absorbent substrate.

The present alkyl polyglycosides are particularly useful for inhibiting the production of bacterial exotoxins when incorporated as part of non-absorbent products. For example, the incorporation of alkyl polyglycoside onto an outer surface of a non-absorbent product, such as an incontinence device, can be very effective. The non-absorbent products are exemplified herein in connection with incontinence or contraceptive devices but would be understood by persons skilled in the art to be applicable to other disposable non-absorbent articles where inhibition of exoproteins from Gram positive bacteria would be beneficial.

When employed as part of an incontinence or contraceptive devices or otherwise introduced into a region affecting the vagina, the alkyl polyglycoside preferably is utilized in a manner and amount so as to minimize its effect on the natural vaginal flora. The present alkyl polyglycoside compositions are generally capable of substantially inhibiting the production of exoproteins from Gram positive bacteria, e.g., by reducing the amount of proteins produced by at least about 75% and preferably by at least about 90%.

The alkyl polyglycoside compositions of the present invention may additionally include adjunct components conventionally found in pharmaceutical compositions in their art-established fashion and at their art-established levels. For example, the compositions may contain additional compatible pharmaceutically active materials for combination therapy, such as supplementary antimicrobials, anti-parasitic agents, antipruritics, local anesthetics, or anti-inflammatory agents.

As used herein the term "nonwoven fabric or web" means a web having a structure of individual fibers or threads which are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, and bonded carded web processes. The basis weight of nonwoven fabrics is usually expressed in ounces of material per square yard ("osy") or grams per square meter ("gsm") and the fiber diameters useful are usually expressed in microns. Basis weights can be converted from osy to gsm simply by multiplying the value in osy by 33.91.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. Nos. 4,340,563; 3,692,618; 3,802,817; 3,338,992; 3,341,394; 3,502,763; 3,502,538; and 3,542,615, the disclosures of which are herein incorporated by reference. Spunbond fibers are quenched and generally not tacky when deposited onto a collecting surface. Spunbond fibers are generally continuous and have average diameters frequently larger than 7 microns, typically between about 10 and 20 microns.

As used herein the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly disbursed meltblown fibers. Such a process is disclosed, for example, in U.S. Pat. No. 3,849,241. Meltblown fibers are microfibers which may be continuous or discontinuous and are generally smaller than 10 microns in average diameter.

As used herein "bonded carded webs" or "BCW" refers to nonwoven webs formed by carding processes as are known to those skilled in the art and further described, for example, in U.S. Pat. No. 4,488,928 which is incorporated herein by reference. Briefly, carding processes involve starting with a blend of, for example, staple fibers with bonding fibers or other bonding components in a bulky ball that is combed or otherwise treated to provide a generally uniform basis weight. This web is heated or otherwise treated to activate the adhesive component resulting in an integrated, usually lofty nonwoven material.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer shall include all possible geometrical configurations of the material. These configurations include, but are not limited to isotactic, syndiotactic and random symmetries.

As used herein, the term "hydrophilic" means that the polymeric material has a surface free energy such that the polymeric material is wettable by an aqueous medium, i.e. a liquid medium of which water is a major component. The term "hydrophobic" includes those materials that are not hydrophilic as defined. The phrase "naturally hydrophobic" refers to those materials that are hydrophobic in their chemical composition state without additives or treatments affecting the hydrophobicity. It will be recognized that hydrophobic materials may be treated internally or externally with surfactants and the like to render them hydrophilic.

As used herein, the term "personal care product" refers to diapers, training pants, absorbent underpants, adult incontinence products, sanitary wipes and feminine hygiene products, such as sanitary napkins and tampons, and the like. The term "absorbent medical product" is employed to refer to products such as medical bandages, tampons intended for medical, dental, surgical, and/or nasal use, surgical drapes and the like.

DETAILED DESCRIPTION

The present alkyl polyglycoside compositions, when exposed to *S. aureus* or other Gram positive bacteria in non-absorbent products, can reduce the production of harmful exoproteins. In particular, exposure to the alkyl polyglycoside(s) can inhibit the production of harmful proteins produced by Staphylococcus and/or Streptococcal species.

The present non-absorbent substrates are particularly adapted to be employed in contact with fluids such as menses, blood products and the like. The substrates commonly include an outer layer formed from a hydrophobic material which includes the alkyl polyglycoside disposed so as to contact the fluid the product is designed to be used in conjunction with. For example, the non-absorbent product may be a female incontinence device formed predominantly from a hydrophobic polymeric material, e.g., having an impervious outer layer formed from rubber or other hydrophobic polymeric material.

Alkyl polyglycoside can generally be represented by the formula:

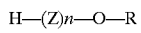

where "Z" is a saccharide residue having 5 or 6 carbon atoms, "n" is a number having a value between 1 and about 6, and "R" represents an alkyl group, typically having 8 to 18 carbon atoms. The "n" represents the average number of saccharide residues in a particular sample of alkyl polyglycoside. Although, as indicated above, the present alkyl polyglycosides can include an oligosaccharide, e.g., where n equals about 4–6, alkyl polyglycosides with a smaller average number of saccharide residues are commonly preferred. Typically, the present alkyl polyglycosides have an "n" which is no more than about 4, preferably no more than about 2 and, more preferably, no more than about 1.5. As defined herein, the term "alkyl polyglycoside" also encompasses alkyl monosaccharides, i.e., where "n" equals 1.

It will be understood that as referred to herein, an "alkyl polyglycoside" may consist of a single type of alkyl polyglycoside molecules or, as is typically the case, may include a mixture of different alkyl polyglycoside molecules. The different alkyl polyglycoside molecules may be isomeric and/or may be alkyl polyglycoside molecules with differing alkyl groups and/or saccharide portions. By the term "alkyl polyglycoside isomers," reference is meant to alkyl polyglycosides which, although including the same alkyl ether residues, may vary with respect to the location of the alkyl ether residue in the alkyl polyglycoside as well as isomers which differ with respect to the orientation of the functional groups about one or more chiral centers in the molecules. For example, an alkyl polyglycoside can include a mixture of molecules with saccharide portions which are mono-, di- or oligosaccharides derived from more than one 6 carbon saccharide residue and where the mono-, di- or oligosaccharide has been etherified by reaction with a mixture of fatty alcohols of varying carbon chain length.

Where more than one saccharide residue is present on average per alkyl polyglycoside molecule (i.e., where "n" is greater than 1), the individual saccharide subunits within the same molecule may be identical or different. Where the individual subunits are not all identical, the order and distribution of subunits is typically random. This is not necessarily the case, e.g., where n=2 and the glycoside includes a specific disaccharide, such as sucrose or fructose. It will be understood that the alkyl polyglycoside may include a mixture of different alkyl polyglycoside molecules and/or a mixture of alkyl polyglycoside isomers. Generally, the present alkyl polyglycosides comprise a mixture of alkyl polyglycoside molecules have alkyl groups with varying chain lengths and include a distribution of mono-, di- and oligosaccharides. For example, the alkyl polyglycosides can include a distribution of mono-, di- and oligosaccharides made up of glucosyl residues. The "alkyl group" portion of the alkyl polyglycosides is generally a linear alkyl group (i.e., a straight chain alcohol residue), typically having an even number of carbon atoms. The present alkyl polyglycosides preferably include alkyl groups having from about 8 to 14 carbon atoms and/or where the average number of carbon atoms in the alkyl chain is 8 to 14 and, preferably, 9 to 11. One example of a suitable alkyl polyglycoside is a mixture of alkyl polyglycoside molecules with alkyl chains having 8 to 10 carbon atoms.

The alkyl polyglycosides can also be characterized in terms of their hydrophilic/lipophilic balance ("HLB"). This can be calculated based on their chemical structure using techniques well known to those skilled in the art. The HLB of the alkyl polyglycosides used in the present methods typically falls within the range of about 10 to about 15. Preferably, the present alkyl polyglycosides have an HLB of at least about 12 and, more preferably, about 12 to 14.

Alkyl polyglycosides in general are known to have excellent surface tension reduction, wetting and dispersant properties. Alkyl polyglycosides can be produced using conventional methodology. For example, U.S. Pat. Nos. 5,527,892 and 5,770,543, the disclosure of which is herein incorporated by reference, describe alkyl polyglycosides and/or methods for their preparation. Since alkyl polyglycosides are derived from saccharides and fatty alcohols, these compounds are readily biodegradable.

Commercially available examples of suitable alkyl polyglycosides include Glucopon 220, 225, 425, 600 and 625, all available from Henkel Corporation. These products are all mixtures of alkyl mono- and oligoglucopyranosides with alkyl groups based on fatty alcohols derived from coconut and/or palm kernel oil. Glucopon 220, 225 and 425 are examples of particularly suitable alkyl polyglycosides. Glucopon 220 is an alkyl polyglycoside which contains an average of 1.4 glucosyl residues per molecule and a mixture of 8 and 10 carbon alkyl groups (average carbons per alkyl chain—9.1). Glucopon 225 is a related alkyl polyglycoside with linear alkyl groups having 8 or 10 carbon atoms (average alkyl chain—9.1 carbon atoms) in the alkyl chain. Glucopon 425 includes a mixture of alkyl polyglycosides which individually include an alkyl group with 8, 10, 12, 14 or 16 carbon atoms (average alkyl chain—10.3 carbon atoms). Glucopon 600 includes a mixture of alkyl polyglycosides which individually include an alkyl group with 12, 14 or 16 carbon atoms (average alkyl chain 12.8 carbon atoms). Glucopon 625 includes a mixture of alkyl polyglycosides which individually include an alkyl group having 12, 14 or 18 carbon atoms (average alkyl chain 12.8 carbon atoms). Another example of a suitable commercially available alkyl polyglycoside is TL 2141, a Glucopon 220 analog available from ICI.

Vaginal tampons suitable for use in this invention are usually made of absorbent fibers, including natural and synthetic fibers, compressed into a unitary body of a size which may easily be inserted into the vaginal cavity. The tampons are normally made in an elongated cylindrical form, but may be made in a variety of shapes. The tampon may or may not be compressed, although compressed types are now generally preferred. The tampon may be made of various fiber blends including both absorbent and nonabsorbent fibers, which may or may not have a suitable cover or wrapper. The cover or wrapper for absorbent products, such as tampons and sanitary napkins, is often made from a sheet of spunbonded fibers, e.g., a spunbond polypropylene sheet.

In one embodiment, the present absorbent product includes a cover sheet which typically contains at least about 3 wt. %, preferably no more than about 16 wt. % and, more preferably, about 5 to about 10 wt. % alkyl polyglycoside (as add-on wt. %). A suitable example of such as non-absorbent product is a pledget having a cover sheet which includes the alkyl polyglycoside. Typically, such a pledget would have a cover sheet formed from spunbond fibers of a hydrophobic polymeric material, e.g., a spunbond polypropylene cover layer, with the alkyl polyglycoside coated on the outside of the fibers. As used herein, the term "pledget" means a compress used to apply pressure or press upon a body part.

The fibers from which the present absorbent products are made may be produced, for example, by the meltblowing or spunbonding processes, including those producing bicomponent, biconstituent or polymer blend fibers which are well known in the art. These processes generally use an extruder to supply melted thermoplastic polymer to a spinneret where the polymer is fiberized to yield fibers which may be staple length or longer. The fibers are then drawn, usually pneumatically, and deposited on a moving foraminous mat or belt to form the nonwoven fabric. The fibers produced in the spunbond and meltblown processes are microfibers as defined above. The manufacture of spunbond and meltblown webs is discussed generally above.

As mentioned, the nonwoven also may be a bonded carded web. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable bonding method, particularly when using bicomponent staple fibers, is through-air bonding.

The present absorbent products contain an effective amount of the inhibiting alkyl polyglycoside compound to substantially inhibit the formation of exoproteins such as TSST-1 when the absorbent product, such as a tampon or sanitary napkin, is exposed to Gram positive bacteria. Where the alkyl polyglycoside is present as part of an absorbent layer of an absorbent product, at least about 0.005 millimoles of alkyl polyglycoside compound per gram of absorbent will generally be effective for reducing exoprotein production. Preferably, the alkyl polyglycoside compound includes at least about 0.05 millimoles per gram of absorbent and, more preferably, about 0.1 millimoles per gram of absorbent to about 1.0 millimoles per gram of absorbent. Although "compound" is used in the singular, one skilled in the art would understand that it includes the plural. That is, the absorbent article can include more than one alkyl polyglycoside compound.

It is generally not necessary to impregnate the entire body of non-absorbent product with the inhibitory agent. Optimum results both economically and functionally, can often be obtained by concentrating the material on or near an outer surface where it will be most effective during use.

An exemplary absorbent material is a nonwoven web composed of 3.0 denier polyethylene 5 sheath/polypropylene core bicomponent staple fibers having a length of 38 millimeters. Such bicomponent fibers can obtained from Chisso Corporation and are typically supplied with a vendor fiber finish. The staple fibers can be sent through an opener and uniformly mixed together before being carded into a web at a line speed of 15.24 meters per minute (50 feet per minute). Once the web was formed, it can be sent through a through-air bonder (drum type) with an air temperature of 131° C. Typical dwell times within the bonder are between 3 and 4.5 seconds. The resultant web, which has a basis weight of 100 gsm and a density of 0.06 gm/cm$^3$, can then wound up on a roll.

Other suitable absorbent materials include materials which include hydrophilic natural and/or synthetic fibers. For example, a material formed from a mixture of cotton and rayon fibers is an absorbent material that can be used to form the absorbent core of absorbent products such as tampons and sanitary napkins.

The alkyl polyglycoside treating composition may contain other additives as appropriate for the desired result so long as they do not have a major detrimental effect on the activity of the alkyl polyglycoside. Examples of such additives include additional conventional surfactants such as ethoxylated hydrocarbons or ionic surfactants, or co-wetting aids such as low molecular weight alcohols. As mentioned, the composition is desirably applied from high solids, advantageously 80% or less solvent or water, so as to minimize drying and its attendant costs and deleterious effects. The treating composition may be applied in varying amounts depending on the desired results and application. The alkyl polyglycoside is generally present in at least about 3 wt. % and more typically about 6 to about 10 wt. % add-on weight based on the weight of an outer layer of a non-absorbent substrate. In some instances, it may be useful to employ higher levels of the alkyl polyglycoside, e.g., up to about 20 wt. % of an outer layer (add-on). For incontinence device applications, for example, effective results may be obtained within a range of about 5% to about 15% alkyl polyglycoside solids add-on based on the dry weight of an outer layer. As used herein, the term "add-on wt. %" refers to the amount of alkyl polyglycoside employed as a percentage of the dry weight of the uncoated substrate. Thus, 10 wt. % (add-on) is equal to 9.1 wt. % based on the total weight of the coated substrate (10/110=9.1). Unless otherwise explicitly stated herein, all amounts of alkyl polyglycoside on a substrate are stated in terms of add-on wt. %, even though often simply referred to as "wt. %". This is not the case for amounts of alkyl polyglycoside present as part of a fluid composition, where the amounts are stated in mmolar or wt. % as a percentage of the total composition.

As will be recognized by those skilled in this art, many substrate materials may be treated in accordance with the invention including nonwovens such as spunbond, meltblown, carded webs and others as well as woven webs and even films and the like where improved fluid distribution is desired. It will also be recognized by those skilled in this art that some alkyl polyglycoside may be used as internal additives, that is, added to the polymer melt directly or in a concentrate form. After fiber formation, such additives can migrate to the fiber surface and impart the desired effect. For further discussion of internal addition of additives, see for example, U.S. Pat. No. 5,540,979, the contents of which are incorporated herein by reference. The substrate basis weight is not critical and may vary widely depending on the application. For sanitary napkin distribution layer applications, spunbond and bonded carded webs are often used with basis weights generally in the range of from about 7 gsm to about 175 gsm.

The compositions may be applied to non-absorbent articles using conventional methods for applying an inhibitory agent to the desired article. For example, devices may be dipped directly into a liquid bath having the agent and then can be air dried, if necessary to remove any volatile solvents. The compositions when incorporated on and/or into the tampon materials may be fugitive, loosely adhered, bound, or any combination thereof. As used herein the term "fugitive" means that the composition is capable of migrating through the tampon materials. For example, the alkylglycoside may be blended together with a polymeric material that is to be processed into a component of an absorbent or non-absorbent product.

Alternatively, an alkyl polyglycoside containing solution may be applied directly onto an individual layer of material before it is incorporated into an article to be manufactured, such as a non-absorbent product. For example, an aqueous solution containing the alkyl polyglycoside can be sprayed onto the surface of a layer of material designed to be incorporated into the non-absorbent product. This can be done either during the production of the individual layer or during a fabrication process which incorporates the layer into the article being manufactured.

Examples of representative personal care product are incontinence or contraceptive devices which includes alkyl polyglycoside. The alkyl polyglycoside may be incorporated into or on an outer layer of the device. Devices with an alkyl polyglycoside, such as Glucopon 220, deposited on the outer layer are particularly suitable for inhibiting the production of bacterial exoproteins by Gram positive bacteria such as *S. aureus*.

Another example of a representative personal care product is a catamenial tampon which includes alkyl polyglycoside. The alkyl polyglycoside may be incorporated into the absorbent portion of the tampon and/or on or in a cover layer. Tampons with an alkyl polyglycoside, such as Glucopon 220, deposited on the cover layer are particularly suitable for inhibiting the production of bacterial exoproteins by Gram positive bacteria such as *S. aureus*.

Another representative personal care product can be in the form of a sanitary napkin structure which includes a distribution layer which incorporates alkyl polyglycoside. The sanitary napkin generally includes an impervious backing, absorbent, distribution ("surge") layer, and cover or body contacting layer. If desired, the absorbent may also be enclosed on its bottom and sides by wrap for enhanced protection against side leakage. Either or all of the cover, distribution or absorbent layers may be treated with alkyl polyglycoside. In a particularly suitable embodiment of the invention, the cover layer is treated with alkyl polyglycoside.

Nonwoven webs coated with alkyl polyglycoside can be prepared by conventional processes. For example, alkyl polyglycoside can be applied to one or both sides of a traveling web. It will be appreciated by those skilled in the art that the application can be carried out as an inline treatment or as a separate, offline treatment step. A web, such as a spunbond or meltblown nonwoven, can be directed over support rolls to a treating station including rotary spray heads for application to one side of web. An optional treating station may include rotary spray heads to apply to alkyl polyglycoside to the opposite side of the web. Each treatment station generally receives a supply of treating liquid from a reservoir. The treated web may then be dried if needed by passing over dryer cans or other drying means and then wound as a roll or converted to the use for which it is intended. Alternative drying apparatus such as ovens, through air dryers, infra red dryers, air blowers, and the like may also be utilized.

The compositions of the present invention can be prepared and applied in other suitable form, including without limitation, aqueous solutions, lotions, balms, gels, salves, ointments, boluses, suppositories, and the like. For example, the active component of the compositions of this invention can be formulated into a variety of formulations such as those employed in current commercial douche formulations, or in higher viscosity douches. For example, the active component of the compositions of this invention can be formulated with surfactants, preferably nonionic surfactants, such as Cremophos RH60, Tween 20 or the like. The compositions of this invention may also contain preservative. Compounds which can impart greater viscosity, such as propylene glycol, may also be added to the compositions of this invention. Generally, higher viscosity compositions are preferred in order to create formulations that will tend to remain in the vagina for a relatively long time period after administration.

The inhibitory alkyl polyglycoside composition may additionally employ one or more conventional pharmaceutically-acceptable and compatible carrier materials useful for the desired application. The carrier can be capable of co-dissolving or suspending the materials used in the composition. Carrier materials suitable for use in the instant composition, therefore, include those well-known for use in the cosmetic and medical arts as a basis for ointments, lotions, creams, salves, aerosols, suppositories, gels and the like. A preferred carrier can be comprised of alcohols and surfactants.

The following examples are presented to illustrate the present invention and to assist one of ordinary skill in making and using the same. The examples are not intended in any way to otherwise limit the scope of the invention.

EXAMPLES

Example A

The effect of Glucopon 220 on growth of *S. aureus* and production of TSST-1 was examined by placing the desired concentration, expressed in millimoles/milliliter (millimolar hereinafter mM), in 100 mL of a growth medium in a sterile, 500 mL Corning fleaker™.

The growth medium was prepared as follows: 37 grams of brain heart infusion broth (BHI) was dissolved in 880 mL distilled water and sterilized. BHI broth is available from Difco™ Laboratories, Becton Dickinson Microbiology Systems, Cockeysville, Md. 21030-0243. The BHI was supplemented with 100 mL fetal bovine serum (FBS) available from Sigma Chemical Company, P.O. Box 14508, St Louis, Mo. 63178-9916. Ten mL of a 0.021 molar sterile solution of the hexahydrate of magnesium chloride (Sigma Chemical Company) was added to the BHI-FBS mixture. Ten mL of a 0.027 molar sterile solution of L-glutamine (Sigma Chemical Company) was also added to the BHI-FBS mixture.

Glucopon 220 was added directly to the growth medium, filter sterilized, and diluted in sterile growth medium to obtain the desired final concentrations.

In preparation for inoculation of the fleakers of growth medium containing Glucopon 220, an inoculating broth was prepared as follows: *S. aureus* MN8 was streaked onto a tryptic soy agar plate (TSA; Difco Laboratories) and incubated at 35° C. The test organism in this example was obtained from Dr. Pat Schlievert, Department of Microbiology, University of Minnesota Medical School, Minneapolis, Minn. After 24 hours of incubation three to five individual colonies were picked with a sterile inoculating loop and used to inoculate the 10 mL of growth medium.

The tube of inoculated growth medium was incubated at 35° C. in atmospheric air. After 24 hours of incubation, the culture was removed from the incubator and mixed well on a S/P brand vortex mixer. A second tube containing 10 mL of the growth medium was inoculated with 0.5 mL of the above 24 hour old culture and incubated at 35° C. in atmospheric air. After 24 hours of incubation the culture was removed from the incubator and mixed well on a S/P brand vortex mixer. The optical density of the culture fluid was determined in a microplate reader (Bio-Tek Instruments, Model EL309, Box 998, Winooski, Vt. 05404-0998). The amount of inoculum necessary to give $5\times10^6$ CFU/mL was determined using a previously prepared standard curve.

The experiment included fleakers of growth medium without Glucopon 220 (control) or with varying concentrations of Glucopon 220. Each fleaker was inoculated with the amount of inoculum determined as described above. The fleakers were capped with sterile aluminum foil and incubated at 35° C. in atmospheric air in a Lab-Line orbital water bath at 180 rpm. The Lab-Line bath was obtained from VWR Scientific Products, 1430 Waukegan Road, McGaw Park, Ill. 60085. Five milliliter samples were removed at the desired time points and the optical density of the culture fluid was determined. The culture fluid was assayed for the number of colony forming units of S. aureus using standard plate count procedures.

After 24 hours of incubation, the experiment was repeated using fresh medium. However, in this instance, the inoculum was from the 24-hour old fleaker containing the same concentration of Glucopon 220. The method described above for determining the amount of fluid necessary to obtain a $5\times10^6$ CFU/mL inoculum was used. For example, S. aureus grown in 2 mM Glucopon 220 were inoculated into fresh growth medium containing 2 mM Glucopon 220. Glucopon 220 was tested at 20, 10, 4, 2, 1, and 0.5 mM concentrations. No growth was observed in the presence of the 10 and 20 mM concentrations. Growth was not observed in the growth medium containing 4 mM Glucopon 220 until 26 hours after inoculation, thus it was not reinoculated into fresh medium after the first 24 hours of incubation.

Five milliliters of the remaining culture fluid was prepared for the analysis of TSST-1 as follows: the culture fluid was centrifuged at 2500 rpm at 2–10° C. for 15 minutes. The supernatant was filter sterilized through an Autovial® 5 syringeless filter, 0.2 uM pore size (Whatman, Inc., Clifton, N.J.). The resulting fluid was frozen at −70° C. in a Fisherbrand® 12×75 mm polystyrene culture tube, Fisher Scientific, 585 Alpha Drive, Pittsburgh, Pa. 15328.

The amount of TSST-1 per mL was determined by a non-competitive, sandwich enzyme-linked immunoabsorbent assay (ELISA). Samples of the culture fluid and the TSST-1 reference standard were assayed in triplicate. The method employed was as follows: four reagents, rabbit polyclonal anti-TSST-1 IgG (LTI-101), rabbit polyclonal anti-TSST-1 IgG conjugated to horseradish peroxidase (#LTC-101), TSST-1 (#TT-606), and normal rabbit serum (NRS) certified anti-TSST-1 free (#NRS-10) were purchased from Toxin Technology, Inc., 7165 Curtiss Avenue, Sarasota, Fla. 34231. A 10 ug/mL solution of the polyclonal rabbit anti-TSST-1 IgG was prepared in phosphate buffered saline (PBS), pH 7.4. The PBS was prepared from 0.016 molar $NaH_2PO_4$, 0.004 molar $NaH_2PO_4$—$H_2O$, 0.003 molar KCl and 0.137 molar NaCl, all available from Sigma Chemical Company. One hundred microliters of the polyclonal rabbit anti-TSST-1 IgG solution was pipetted into the inner wells of polystyrene microplates, catalogue #439454, obtained from Nunc-Denmark. The plates were covered and incubated at room temperature overnight. Unbound anti-toxin was removed by draining until dry.

TSST-1 was diluted to 10 ng/mL in PBS with phosphate buffered saline (pH 7.4) containing 0.05% (vol/vol) Tween-20 (PBS-Tween) available from Sigma Chemical Company and 1% NRS (vol/vol) and incubated at 4° C. overnight. Test samples were combined with 1% NRS (vol/vol) and incubated at 4° C. overnight.

One hundred microliters of a 1% (wt/vol) solution of the sodium salt of casein in PBS (Sigma Chemical Company) was pipetted into the inner wells of polystyrene microplates, the plates were covered, and incubated at 35° C. for one hour. Unbound BSA was removed by 3 washes with PBS-Tween. TSST-1 reference standard (10 ng/mL) treated with NRS, test samples treated with NRS, and reagent controls were pipetted in 200 microliter volumes to their respective wells on the first and seventh columns of the plate. One hundred microliters of PBS-Tween was added to the remaining wells. The TSST-1 reference standard and test samples were then serially diluted 6 times in the PBS-Tween by transferring 100 microliters from well-to-well. The samples were mixed prior to transfer by repeated aspiration and expression. This was followed by incubation for 1.5 hours at 35° C. and five washes with PBS-T and three washes with distilled water to remove unbound toxin.

The rabbit polyclonal anti-TSST-1 IgG conjugated to horseradish peroxidase was diluted according to manufacturer's instructions and 50 microliters was added to each microtiter well, except well A-1, the conjugate control well. The plates were covered and incubated at 35° C. for one hour.

Following incubation, the plates were washed five times in PBS-Tween and three times with distilled water. Following the washes, the wells were treated with 100 microliters of a horseradish peroxidase substrate buffer consisting of 5 mg of o-phenylenediamine and 5 microliters of 30% hydrogen peroxide (both from Sigma Chemical Company) in 11 mL of citrate buffer, pH 5.5. The citrate buffer was prepared from 0.012 anhydrous citric acid and 0.026 molar dibasic sodium phosphate both available from Sigma Chemical Company. The plates were incubated for 15 minutes at 35° C. The reaction was stopped by the addition of 50 microliters of a 5% sulfuric acid solution. The intensity of the color reaction in each well was evaluated using the BioTek Model EL309 microplate reader (OD 490 nm). TSST-1 concentrations in test samples were determined from the reference toxin regression equation derived during each assay procedure.

The efficacy of Glucopon 220 in inhibiting the production of TSST-1 is shown in Table I below. The data is presented in units of TSST-1 (ng/OD units) as well as showing the TSST-1 levels as a percentage of the untreated control.

TABLE I

| Glucopon 220 (mM) | OD (10 hr) | TSST-1 (ng/OD units) | TSST-1 (% of control) | OD (24 hr) | TSST-1 (ng/OD units) | TSST-1 (% of control) |
|---|---|---|---|---|---|---|
| | | First 24 hour incubation | | | | |
| None | 7.49 | 189 | | 11.47 | 1471 | |
| 4 mM | 0.03 | ND | — | 0.04 | ND | — |
| 2 mM | 7.95 | 23 | 12% | 11.47 | 37 | 3% |
| 1 mM | 8.1 | 63 | 33% | 11.21 | 168 | 11% |
| 0.5 mM | 7.45 | 143 | 76% | 10.71 | 187 | 13% |

TABLE I-continued

| Glucopon 220 (mM) | OD (10 hr) | TSST-1 (ng/OD units) | TSST-1 (% of control) | OD (24 hr) | TSST-1 (ng/OD units) | TSST-1 (% of control) |
|---|---|---|---|---|---|---|
| Second 24 hour incubation in fresh medium | | | | | | |
| None | 6.34 | 232 | — | 10.00 | 1141 | — |
| 2 mM | 7.91 | 12 | 8% | 11.93 | 37 | 3% |
| 1 mM | 6.89 | 41 | 17% | 9.92 | 127 | 11% |

Example B

Tampon prototypes with cover sheets treated with a variety of different non-ionic surface treatments were examined in a laboratory microbial challenge test to determine the effect surface treatments on TSST-1 production by *Staphylococcus aureus*.

Cover sheet material was produced by coating the particular non-ionic surface treatment onto a commercially produced 0.4 osy polypropylene spunbond cover material. The surface treatment was applied by diluting the surfactant to the desired concentration with purified water and applying the solution to the nonwoven cover sheet material with a Butterworth treater. The amount of solution applied was controlled by nip pressure and line speed.

The coated cover sheet was used to fabricate tampon prototypes containing an absorbent layer made up of a mixture of cotton and rayon fibers. An uncompressed absorbent pledget made of the combination of cotton and rayon fibers was covered with the treated spunbond cover material. A string hole was punched through the uncompressed pledget. A string was knotted and looped through the absorbent pledget and cover and the resulting construction was compressed and placed in a tampon applicator.

The add-on level of the various cover sheet surface treatments was determined by the weight of extractables. Correction was made for the level of extractables obtained from untreated cover material, extraction efficiency for the particular surfactant and the solids content of the surfactants. The treated spunbond cover sheets were sampled in triplicate and the recovery efficiency was calculated from triplicate testing of one add-on level for each surfactant. As controls, spiked samples were prepared using untreated nonwoven cover sheet material and reference samples of the various surfactants. The spiked samples were subjected to the same extraction conditions as the corresponding coated cover sheet materials.

Tampon prototypes to be tested were randomly selected from each of the groups of protoypes with varying types of cover sheet coating. The prototypes were grasped with sterile forceps. The string was cut off with sterile scissors, and the pledget placed into a sterile, capped polystyrene test tube with the string end down.

Each pledget was inoculated with 10.5 mL of an inoculating broth containing $5\times10^6$ CFU/mL of *S. aureus* MN8 (obtained from Dr. Pat Schlievert, Department of Microbiology, University of Minnesota Medical School, Minneapolis, Minn.). After incubation at 35° C. for 24 hours of in plugged tubes, the pledgets were diluted with sterile fluid and fluid was squeezed by hand pressure out of the pledget.

Assay for TSST-1 Concentration

Five milliliters of the culture fluid was prepared for the analysis of TSST-1 as follows: the culture fluid was centrifuged at 9000 rpm at 4° C. for 5 minutes. The supernatant was filter sterilized through 0.45 micron filter and frozen at −70° C. in two aliquots in 1.5 mL polypropylene screw cap freezer vials.

The amount of TSST-1 per mL was determined by a non-competitive, sandwich enzyme-linked immunoabsorbent assay (ELISA). Samples of the culture fluid and the TSST-1 reference standard were assayed in triplicate. The method employed was as follows: four reagents, rabbit polyclonal anti-TSST-1 IgG (LTI-101), rabbit polyclonal anti-TSST-1 IgG conjugated to horseradish peroxidase (#LTC-101), TSST-1 (#TT-606), and normal rabbit serum (NRS) certified anti-TSST-1 free (#NRS-10) were purchased from Toxin Technology, Inc., 7165 Curtiss Avenue, Sarasota, Fla. 34231. Sixty-two microliters of polyclonal rabbit anti-TSST-1 IgG (#LTI-101) was appropriately diluted so that a 1:100 dilution gave an absorbance of 0.4 at 205 nanometers. This was added to 6.5 mL of 0.5 molar carbonate buffer, pH 9.6, and 100 ul of the solution was pipetted into the inner wells of polystyrene microplates, catalogue #439454, obtained from Nunc-Denmark. The plates were covered and incubated at 37° C. overnight. Unbound anti-toxin was removed by four washes with phosphate buffered saline (pH 7.2) (0.016 molar $NaH_2PO_4$ and 0.9% [wt/vol] NaCl both available from Sigma Chemical Company) containing 0.5% [vol/vol] Tween 20 (PBS-Tween), also available from Sigma Chemical Company in an automatic plate washer. The plates were treated with 100 ul of a 1% [wt/vol] solution of bovine serum albumin (BSA), fraction V, in the 0.5 molar carbonate buffer described above. BSA fraction V is available from Sigma Chemical Company. The plates were covered and incubated at 37° C. for one hour. Unbound BSA was removed by six washes with 250 ul PBS-Tween. Test samples were treated with normal rabbit serum (10% [vol/vol] final concentration) for 15 minutes at room temperature. TSST-1 reference standard, serially diluted from 1–20 ng/mL in PBS-Tween and the NRS treated test samples (serially diluted in PBS-Tween so that the resultant TSST-1 concentration is between 1–20 ng), were pipetted in 100 ul volumes to their respective wells. This was followed by incubation for two hours at 37° C. and four washes of 250 mL PBS-Tween to remove unbound toxin. The rabbit polyclonal anti-TSST-1 IgG conjugated to horseradish peroxidase was diluted according to manufacturer's instructions. The final use dilution of the conjugate was determined by running standard curves of TSST-1 reference standard with the conjugate at undiluted, 1:2 and 1:4 dilutions. The dilution that gave results most comparable to previous lots of conjugate was selected. One hundred microliter volumes of this dilution was added to each microtiter well. The plates were covered and incubated at 37° C. for one hour.

Following incubation the plates were washed six times in 250 ul PBS-Tween and three times with distilled water. Following the washes, the wells were treated with 100 ul of a horseradish peroxidase substrate solution consisting of 0.015 molar sodium citrate (pH 4.0), 0.6 millimolar 2,2'-Azino-bis-(3-ethylbenzthiazoline-6-sulfonic acid) diammonium salt and 0.009% (vol/vol) hydrogen peroxide, all available from Sigma Chemical Company. The intensity of the color reaction in each well was evaluated over time using a BioTek Model EL340 Microplate reader (OD 405 nm) and Kineticalc® software available from Biotek Instruments, Inc. TSST-1 concentrations in test samples derived from the reference toxin regression equations for each assay procedure.

The efficacy of Glucopon 220 in inhibiting the production of TSST-1 is shown in Table II below.

TABLE II

| Surface Treatment | Amount (Wt. % Solids) | TSST-1 (ng/mL) | Final [*S. aureus*] (× 10⁹ CFU/ml) |
|---|---|---|---|
| Laureth-4 | 7 wt. % | 531.8 | 4.57 |
| PPG-5 Laureth-5 | 18 wt. % | 609.2 | 3.82 |
| Glucopon 220 | 3 wt. % | 554.8 | 6.41 |
| Glucopon 220 | 14 wt. % | 327.5 | 6.99 |
| Steareth-2 | 8 wt. % | 680.7 | 5.76 |

Example C—Intake Data

Cover sheet material similar to that used to produce a tampon was prepared by coating a solution containing the designated amount (on a solids basis) of the chosen non-ionic surface treatment onto a polypropylene spunbond web (0.4 osy). The solutions were prepared with HPLC grade water except in the case of Steareth-2 which was dissolved in HPLC grade water containing 3 wt. % hexanol. The spunbond material was coated at a line speed of 75 fpm. The sample was then dried (dry can temperature—225° F.) before use and cut into four or eight inch lengths. Table III below shows the concentrations of the solutions, wet pick up levels and nip pressures used to coat the spunbond cover sheet material with the various surface treatments.

TABLE III

| Surfactant | Target Wet Pick Up (wt. %) | Nip Pressure |
|---|---|---|
| 3% Glucopon 220 | 100% | 7 psi |
| 12% Glucopon 220 | 100% | 8 psi |
| 9% Laureth-4 | 100% | 8 psi |
| 8.7% PPG-5 Laureth-5 | 150% | 4 psi |
| 3% Steareth-2 | 200% | 3 psi |

An absorbent ribbon formed from a blend of 2/3 rayon and 1/3 cotton fibers was prepared and cut into 4 inch lengths. Four inch lengths of the treated spunbond web were placed over a 4 inch piece of the rayon/cotton absorbent. Each sample was than subjected to three insults of 0.25 mL of a low viscosity menses simulant similar to that described in International Patent Application WO 98/09662. The insults were delivered at a rate of 2.5 mL/min at intervals of three minutes. The intake time (in seconds) for the simulated menses to pass into the cover sheet sample was recorded for each insult. The results are shown in Table IV below.

TABLE IV

| | Conc. | Intake Time (sec) | | |
|---|---|---|---|---|
| Surfactant | (wt. %) | First | Second | Third |
| Glucopon 220 | 3% | 6.97 | 8.87 | 10.84 |
| Glucopon 220 | 6% | 6.85 | 8.73 | 9.70 |
| Glucopon 220 | 9% | 6.78 | 7.78 | 8.13 |
| Glucopon 220 | 13% | 6.90 | 7.95 | 8.23 |
| Laureth-4 | 3% | 6.71 | 7.74 | 8.27 |
| Laureth-4 | 6% | 6.82 | 8.01 | 8.56 |
| Laureth-4 | 9% | 6.51 | 7.27 | 7.59 |
| Laureth-4 | 13% | 6.51 | 7.46 | 7.97 |
| PPG-5 Laureth-5 | 3% | 6.53 | 7.47 | 7.93 |
| PPG-5 Laureth-5 | 6% | 6.84 | 8.18 | 8.84 |
| PPG-5 Laureth-5 | 9% | 7.10 | 8.39 | 8.82 |
| PPG-5 Laureth-5 | 13% | 6.96 | 7.79 | 8.07 |
| Steareth-2 (IPA) | 3% | 33.42 | 8.61 | 9.38 |

TABLE IV-continued

| | Conc. | Intake Time (sec) | | |
|---|---|---|---|---|
| Surfactant | (wt. %) | First | Second | Third |
| Steareth-2 (IPA) | 6% | 7.13 | 8.37 | 9.21 |
| Steareth-2 (Hexanol) | 6% | 7.81 | 8.38 | 10.79 |

Example D—Distribution Test

Cover sheet material similar to that used to produce a tampon was prepared by spraying a solution containing the designated amount (on a solids basis) of the chosen non-ionic treatment onto a 0.4 osy polypropylene spunbond web (see description in Example C). The sample was then dried in an oven before use and cut into eight inch lengths. An absorbent ribbon formed from a blend of 2/3 rayon and 1/3 cotton fibers was prepared and cut into eight inch lengths.

Eight inch lengths of the treated sample were weighed and each placed individually over an eight inch piece of the rayon/cotton absorbent. The treated cover sheet was then insulted with 5 mL of a low viscosity menses solution at a rate of 10 mL/hr. The absorbent layer was then cut into eight one inch pieces and each sample was weighed to obtain a saturation profile of the particular treated sample. The fluid distribution was obtained by calculating the degree of saturation (amount liquid absorbed) for each one inch segment of a particular sample. For a given sample, a distribution profile can be constructed by adding the individual saturation segments together. The fluid distribution can be used to calculate a Saturation Ratio ("SR") for a given 8 inch absorbent strip. In the formula for "SR" shown below, each of the letters "A" through "H" represents the amount of liquid absorbed in a given one inch segment of the eight inch strip where the segments are labeled alphabetically (A–H) running consecutively from one end to the other of the strip.

$$SR=[(4*A)+(4*H)]/(D+E)+[(4*A)+(4*G)]/(D+E)+[(2*C)+(2*F)]/(D+E)$$

This method gives the highest weighting to a sample which evenly distributes a fluid over the entire eight inch length of the test strip. The ratio is calculated in the same manner as torque, where the fluid in each section is multiplied by the distance wicked by the fluid. This ratio gives higher values to materials which wick fluid the farthest. Due to the weighting used in the method, the SR evaluation scale will provide different values for samples of the same material of varying length. For samples of constant length, the specimen with the highest SR value distributes fluid the most effectively.

The Saturation Ratio as defined above, for each treated sample (at a variety of non-ionic add on levels) is shown in Table V below. There did not appear to be any significant differences for any of the non-ionic treatment examined as a function of concentration for each non-ionic treatment examined. A second method was used to corroborate the results obtained by the "SR" method. The average and standard deviation of the eight segments was calculated. The coefficient of variance ("COV"—standard deviation divided by the average) was then calculated for the eight segments. A COV value of "0" signifies that there were equal amounts of fluid in each of the eight segments, i.e., a perfectly flat distribution of fluid. Thus, for the "SR" method a higher value indicates better wicking performance, while the reverse is true for the COV-DSN test.

TABLE V

| Surfactant | Conc. (wt. %) | Sat. Ratio | COV-DSN |
|---|---|---|---|
| Laureth-4 | 3% | 1.51 | 4.11 |
| Laureth-4 | 6% | 1.51 | 4.11 |
| Laureth-4 | 9% | 1.51 | 4.11 |
| Laureth-4 | 13% | 1.51 | 4.11 |
| Glucopon 220 | 3% | 1.48 | 4.17 |
| Glucopon 220 | 6% | 1.48 | 4.17 |
| Glucopon 220 | 9% | 1.48 | 4.17 |
| Glucopon 220 | 13% | 1.48 | 4.17 |
| PPG-5 Laureth-5 | 3% | 1.62 | 4.12 |
| PPG-5 Laureth-5 | 6% | 1.62 | 4.12 |
| PPG-5 Laureth-5 | 9% | 1.62 | 4.12 |
| PPG-5 Laureth-5 | 13% | 1.62 | 4.12 |
| Steareth-2 (IPA) | 3% | 1.06 | 4.18 |
| Steareth-2 (IPA) | 9% | 1.62 | 4.18 |
| Steareth-2 (Hexanol) | 6% | 0.83 | 4.55 |

Example E

The effect of Glucopon 220 on growth of *S. aureus* and production of alpha-toxin (alpha-hemolysin) was determined by placing the desired concentration, expressed in millimoles/milliliter (millimolar hereinafter mM), in 100 mL of a growth medium in a sterile, 500 mL Corning fleaker™. Glucopon 220 was added directly to the growth medium, filter sterilized, and diluted in sterile growth medium to obtain the desired final concentrations.

The experiment was conducted following the procedure described in Example A except that the test organism in this example, *S. aureus* RN6390, was obtained from Dr. Richard Novick, The Skirball Institute for Biomolecular Medicine, New York University Medical Center, New York, N.Y. The experiment included fleakers of growth medium without Glucopon 220 (control) or with varying concentrations of Glucopon 220. Each fleaker was inoculated with *S. aureus* RN6390 following the procedure described in Example A. The fleakers were capped with sterile aluminum foil and incubated at 35° C. for 24 hours in atmospheric air in a Lab-Line orbital water bath at 180 rpm.

Five milliliters of the culture fluid was prepared for the analysis of alpha-hemolysin as follows: the culture fluid was adjusted to a standard absorbance (1.0) and centrifuged at 2500 rpm at 2–10° C. for 15 minutes. The supernatant was filter sterilized through an Autovial® 5 syringeless filter, 0.2 micron pore size (Whatman, Inc., Clifton, N.J.). The resulting fluid was frozen at −20° C. in a Fisherbrand® 12×75 mm polystyrene culture tube, Fisher Scientific, 585 Alpha Drive, Pittsburgh, Pa. 15328.

The amount of alpha-hemolysin was determined by a hemolytic assay using rabbit red blood cells. The method employed was as follows: defibrinated rabbit red blood cells (rrbc; Remel) were washed 3 times in a Tris-saline buffer consisting of 50 mM Tris/Tris-HCl and 100 mM NaCl, pH 7.0. Centrifugation was at 800×g for 7 minutes. The reagents were obtained from Sigma Chemical Corporation. The rrbc were suspended in 200 mL Tris-saline buffer to a concentration of 0.5%. The culture supernatants were serially diluted in the culture medium. One part diluted sample was combined with 9 parts rrbc. All sample assays were run in triplicate. Controls for hemolysis consisted of a negative control (one part Tris-saline buffer to 9 parts rrbc) and a positive control (one part 10% SDS to 9 parts rrbc). Ten replicas of the controls were prepared. All assay samples were incubated at 37° C. for 30 minutes, then centrifuged at 800×g for 10 minutes. The amount of hemolysis in the samples and controls was measured at 405 nm in a BioTek Model EL309 microplate reader. Units of activity are expressed as the reciprocal of the dilution of each test sample giving 50% lysis.

The effect of Glucopon 220 on alpha-toxin production is shown in Table VI below.

TABLE VI

| Glucopon 220 (mM) | Alpha-hemolysin units | Alpha hemolysin (% of control) |
|---|---|---|
| None | 32 | |
| 2 mM | 0 | 0.0% |
| 1 mM | 2.2 | 6.9% |
| 0.5 mM | 4.4 | 13.8% |

Throughout this application various publications are referenced. The disclosures of these publications in their entireties are hereby incorporated by reference into this application in order to more fully describe the state of the art to which this invention pertains.

The invention has been described with reference to various specific and illustrative embodiments and techniques. However, it should be understood that many variations and modifications may be made while remaining within the spirit and scope of the invention.

What is claimed is:

1. An exoprotein inhibitor for inhibiting the production of exoproteins from Gram positive bacteria comprising a non-absorbent substrate suitable for insertion into a vagina having deposited thereon an amount of alkyl polyglycoside effective for inhibiting production of exoprotein from Gram positive bacteria, said alkyl polyglycoside having an alkyl group with an average of 8 to 14 carbon atoms, wherein the non-absorbent substrate is Selected from the group consisting of a non-absorbent incontinence device, a barrier birth control device, a contraceptive sponge, a tampon applicator, and a douche.

2. The exoprotein inhibitor of claim 1 comprising an amount of the alkyl polyglycoside effective for inhibiting production of TSST-1 from *Staphylococcus aureus*.

3. The exoprotein inhibitor of claim 1 comprising an amount of the alkyl polyglycoside effective for inhibiting production of alpha-toxin from *Staphylococcus aureus*.

4. The exoprotein inhibitor of claim 1 wherein the alkyl polyglycoside has an alkyl group having from 8 to 18 carbon atoms.

5. The exoprotein inhibitor of claim 1 wherein the alkyl group is a linear alkyl group.

6. The exoprotein inhibitor of claim 5 wherein the alkyl polyglycoside has an alkyl group with 8 to 14 carbon atoms.

7. The exoprotein inhibitor of claim 1 wherein the alkyl polyglycoside is an alkyl polyglucoside.

8. The exoprotein inhibitor of claim 1 wherein the alkyl polyglycoside has an HLB of 10 to 15.

9. The exoprotein inhibitor of claim 1 wherein the alkyl polyglycoside is represented by:

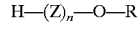

wherein "Z" is a saccharide residue having 5 or 6 carbon atoms, "n" is a number having a value greater than 1, and "R" represents a linear alkyl group having 8 to 14 carbon atoms.

10. The exoprotein inhibitor of claim 9 wherein the "Z" is a glucosyl residue.

11. The exoprotein inhibitor of claim 1 wherein the alkyl polyglycoside has an alkyl group with an average number of 9 to 11 carbon atoms.

12. The exoprotein inhibitor of claim 1 wherein the alkyl polyglycoside has a linear alkyl chain having 8 to 10 carbon atoms.

13. The exoprotein inhibitor as set forth in claim 1 further comprising a surface active agent selected from the group consisting of myreth-3-myristate, glycerol monolaurate, and laureth-4.

14. An exoprotein inhibitor for inhibiting the production of exoproteins from Gram positive bacteria comprising a tampon applicator, a surface active agent selected from the group consisting of myreth-3-myristate, glycerol monolaurate, and laureth-4, and from about 5 wt. % to about 10 wt. % of an alkyl polyglycoside, said alkyl polyglycoside being effective for inhibiting the production of exoprotein from Gram positive bacteria, and said alkyl polyglycoside having a linear alkyl group with 8 to 14 carbon atoms.

15. The exoprotein inhibitor as set forth in claim 14 wherein the alkyl polyglycoside has an HLB of 10 to 15.

16. An exoprotein inhibitor for inhibiting the production of exoproteins from Gram positive bacteria comprising an incontinence device, a surface active agent selected from the group consisting of myreth-3-myristate, glycerol monolaurate, and laureth-4, and from about 5 wt. % to about 10 wt. % of an alkyl polyglycoside, said alkyl polyglycoside being effective for inhibiting the production of exoprotein from Gram positive bacteria, and said alkyl polyglycoside having a linear alkyl group with 8 to 14 carbon atoms.

17. The exoprotein inhibitor as set forth in claim 16 wherein the alkyl polyglycoside has an HLB of 10 to 15.

18. An exoprotein inhibitor for inhibiting the production of exoproteins from Gram positive bacteria comprising a barrier birth control device, a surface active agent selected from the group consisting of myreth-3-myristate, glycerol monolaurate, and laureth-4, and from about 5 wt. % to about 10 wt. % of an alkyl polyglycoside, said alkyl polyglycoside being effective for inhibiting the production of exoprotein from Gram positive bacteria, and said alkyl polyglycoside having a linear alkyl group with 8 to 14 carbon atoms.

19. The exoprotein inhibitor as set forth in claim 18 wherein the alkyl polyglycoside has an HLB of 10 to 15.

20. An exoprotein inhibitor for inhibiting the production of exoproteins from Gram positive bacteria comprising a contraceptive sponge, a surface active agent selected from the group consisting of myreth-3-myristate, glycerol monolaurate, and laureth-4, and from about 5 wt. % to about 10 wt. % of an alkyl polyglycoside, said alkyl polyglycoside being effective for inhibiting the production of exoprotein from Gram positive bacteria, and said alkyl polyglycoside having a linear alkyl group with 8 to 14 carbon atoms.

21. The exoprotein inhibitor as set forth in claim 20 wherein the alkyl polyglycoside has an HLB of 10 to 15.

* * * * *

UNITED STATES PATENT AND TRADEMARK OFFICE
CERTIFICATE OF CORRECTION

PATENT NO. : 6,676,957 B1
DATED : January 13, 2004
INVENTOR(S) : Resheski-Wedepohl et al.

It is certified that error appears in the above-identified patent and that said Letters Patent is hereby corrected as shown below:

Column 1,
Line 30, "contact" should read -- contract --.
Line 50, "by," should read -- by --.

Column 2,
Line 19, "an" should read -- a --.
Lines 38-39, "suitable a non-absorbent" should read -- suitable non-absorbent --.
Line 42, "women's" should read -- woman's --.
Line 59, "contact" should read -- contact with --.

Column 3,
Line 8, ""devices" should read -- device --.

Column 4,
Line 36, "polymer" should read -- "polymer" --.

Column 5,
Line 61, "have" should read -- having --.
Line 67, "alcolhol" should read -- alcohol --.

Column 6,
Line 67, "such as" should read -- such a --.

Column 7,
Line 65, "can" should read -- can be --.

Column 8,
Line 8, "wound" should read -- be wound --.

Column 9,
Line 56, "of web." should read -- of the web. --.
Line 67, "form," should read -- forms, --.

Column 10,
Line 48, "St" should read -- St. --.

UNITED STATES PATENT AND TRADEMARK OFFICE
CERTIFICATE OF CORRECTION

PATENT NO. : 6,676,957 B1
DATED : January 13, 2004
INVENTOR(S) : Resheski-Wedepohl et al.

It is certified that error appears in the above-identified patent and that said Letters Patent is hereby corrected as shown below:

<u>Column 13,</u>
Line 17, "effect" should read -- effect of --.
Line 61, "of" should be deleted.

<u>Column 15,</u>
Line 44, "than" should read -- then --.

<u>Column 16,</u>
Line 29, "(amount liquid" should read -- (amount of liquid --.

<u>Column 18,</u>
Line 34, "Selected" should read -- selected --.

Signed and Sealed this

Eighth Day of June, 2004

JON W. DUDAS
*Acting Director of the United States Patent and Trademark Office*